United States Patent
Park et al.

(10) Patent No.: US 12,310,694 B2
(45) Date of Patent: May 27, 2025

(54) REAL-TIME MULTI-MONITORING APPARATUS AND METHOD USING ELECTROCARDIOGRAPH

(71) Applicant: MEZOO CO., LTD., Wonju-si (KR)

(72) Inventors: Jung Hwan Park, Wonju-si (KR); SungPil Cho, Wonju-si (KR); Jun Hyun Park, Wonju-si (KR); Eunhye Kim, Taebaek-si (KR); Hun Shim, Wonju-si (KR); Hyun Seok Choi, Wonju-si (KR); Junkyu Lee, Wonju-si (KR)

(73) Assignee: MEZOO CO., LTD., Wonju-si (KR)

( * ) Notice: Subject to any disclaimer, the term of this patent is extended or adjusted under 35 U.S.C. 154(b) by 347 days.

(21) Appl. No.: 17/972,756

(22) Filed: Oct. 25, 2022

(65) Prior Publication Data

US 2023/0038108 A1 Feb. 9, 2023

Related U.S. Application Data

(63) Continuation of application No. PCT/KR2021/018979, filed on Dec. 14, 2021.

(30) Foreign Application Priority Data

Feb. 24, 2021 (KR) ........................ 10-2021-0025134
Aug. 10, 2021 (KR) ........................ 10-2021-0105379

(51) Int. Cl.
*A61B 5/346* (2021.01)
*A61B 5/00* (2006.01)
*G16H 40/67* (2018.01)

(52) U.S. Cl.
CPC ............ *A61B 5/0006* (2013.01); *A61B 5/346* (2021.01); *A61B 5/725* (2013.01); *G16H 40/67* (2018.01)

(58) Field of Classification Search
CPC ......... A61B 5/0006; A61B 5/28; A61B 5/346; A61B 5/725; G16H 40/67; G16H 50/70
See application file for complete search history.

(56) References Cited

U.S. PATENT DOCUMENTS

| 2007/0032733 A1 | 2/2007 | Burton |
| 2009/0063187 A1 | 3/2009 | Johnson et al. |

(Continued)

FOREIGN PATENT DOCUMENTS

| JP | 2004147993 A | 5/2004 |
| JP | 2007517553 A | 7/2007 |

(Continued)

OTHER PUBLICATIONS

International Search Report—PCT/KR2021/018979 dated Mar. 17, 2022.

*Primary Examiner* — George Manuel
(74) *Attorney, Agent, or Firm* — CANTOR COLBURN LLP

(57) ABSTRACT

Provided is a real-time multi-monitoring method using an electrocardiograph and a real-time multi-monitoring method using an electrocardiograph including connecting at least one of a plurality of electrocardiographs via a network; receiving identification information of a user which is linked to an electrocardiograph to identify the plurality of electrocardiographs; collecting biometric signal information from the plurality of electrocardiographs; and analyzing a health condition in consideration of predetermined reference information which is defined for each user and biometric signal information collected from each of the plurality of electrocardiographs.

6 Claims, 3 Drawing Sheets

(56) References Cited

U.S. PATENT DOCUMENTS

| | | | |
|---|---|---|---|
| 2009/0264784 A1 | 10/2009 | Stasz | |
| 2013/0317377 A1 | 11/2013 | Gupta et al. | |
| 2014/0249855 A1* | 9/2014 | Moore | G16H 15/00 |
| | | | 705/3 |
| 2017/0146390 A1 | 5/2017 | Kovacs | |
| 2020/0022604 A1* | 1/2020 | Scabellone | G16H 50/20 |

FOREIGN PATENT DOCUMENTS

| | | |
|---|---|---|
| JP | 2014100473 A | 6/2014 |
| JP | 2016013196 A | 1/2016 |
| JP | 6764103 B1 | 9/2020 |
| KR | 20080059369 | 6/2008 |
| KR | 20100050616 | 5/2010 |
| KR | 101002020 | 12/2010 |
| KR | 20190132826 | 11/2019 |
| KR | 102134206 | 7/2020 |
| KR | 102154763 | 9/2020 |
| WO | 2005067790 A1 | 7/2005 |
| WO | 2007131064 A2 | 11/2007 |
| WO | 2012117316 A2 | 9/2012 |
| WO | 2017009880 A1 | 1/2017 |

\* cited by examiner

REAL-TIME MULTI-MONITORING APPARATUS AND METHOD USING ELECTROCARDIOGRAPH

TECHNICAL FIELD

The present disclosure relates to real-time multi-monitoring apparatus and method using an electrocardiograph.

BACKGROUND ART

Recently, in accordance with the development of information and communication technology in the medical industry, systems that can monitor the patient's condition in real-time by attaching various electronic devices to the patient have emerged in order to actively respond to emergency medical situations. In particular, a patient who encounters an emergency situation or is unstable is mostly unprotectable, and it is practically difficult to observe the patient by the medical personnel who is stationed. Accordingly, this system immediately responds to the emergency situations to enable the systematic management of the patients.

However, when various wired electronic devices are directly attached on a body of the patient, it is inconvenient by restricting the patient's basic activities, such as going to the bathroom or the medical office or moving hands or feet on the bed.

A related art of the present disclosure is disclosed in Korean Registered Patent Publication No. 10-1002020.

DISCLOSURE

Technical Problem

The present disclosure has made an effort to solve the problems of the related art and an object is to provide real-time multi-monitoring apparatus and method using an electrocardiograph which allow watching biosignals measured by the electrocardiograph and events related thereto in real time, and can monitor many patients in real-time.

However, objects to be achieved by various embodiments of the present disclosure are not limited to the technical objects as described above and other technical objects may be present.

Technical Solution

As a technical means to achieve the above-described technical object, according to an aspect of the present disclosure, a real-time multi-monitoring method using an electrocardiograph may include connecting at least one of a plurality of electrocardiographs via a network; receiving identification information of a user which is linked to an electrocardiograph to identify the plurality of electrocardiographs; collecting biometric signal information from the plurality of electrocardiographs; and analyzing a health condition in consideration of predetermined reference information which is defined for each user and biometric signal information collected from each of the plurality of electrocardiographs.

Further, in the connecting via the network, at least one of the plurality of electrocardiographs which is attached to a part of a body of the user who is required to be monitored to measure biometric signal information is connected, and the connected electrocardiograph is changed to a connected state and may transmit the biometric signal information which is collected in response to the connected state.

Further, in the connecting via the network, a communication enable state or disable state of the network with at least one of the plurality of electrocardiographs is determined and when the determination result is a communication disable state of the network, the electrocardiograph may transmit the collected biometric signal information to a user terminal linked to the electrocardiograph.

Further, in the analyzing of a health condition, when there is a waveform which satisfies a predetermined feature condition in the acquired biometric signal information, it is determined that a signal corresponding to the waveform which satisfies the predetermined feature condition is a suspicious abnormal electrocardiogram (ECG) signal, and it is determined whether the suspicious abnormal ECG signal may be an abnormal ECG signal based on the comparison of similarity between waveform data of the plurality of abnormal ECG signals which is stored in advance in the database and waveform data of the suspicious abnormal ECG signal.

Here, the predetermined reference information which is defined for each user may be a default setting value generated so as to correspond to each of the plurality of activity modes by standardizing the plurality of biometric information of the user collected for a predetermined time.

According to an aspect of the present disclosure, a real-time multi-monitoring apparatus using an electrocardiograph may include a communication unit which is connected to at least one of a plurality of electrocardiographs via a network; a receiving unit which receives identification information of a user which is linked to an electrocardiograph to identify the plurality of electrocardiographs; a collecting unit which collects biometric signal information from the plurality of electrocardiographs; and an analyzing unit which analyzes a health condition in consideration of predetermined reference information which is defined for each user and biometric signal information collected from each of the plurality of electrocardiographs.

The above-described solving means are merely illustrative, and should not be construed as limiting the present disclosure. In addition to the above-described exemplary embodiments, additional embodiments may be further provided in the drawings and the detailed description of the present disclosure.

Advantageous Effects

According to the above-described technical solution of the present disclosure, it is possible to monitor patients at a glance in the hospital by a system which is capable of simultaneously measuring and multi-monitoring biosignals in real-time.

However, the effect which can be achieved by the present disclosure is not limited to the above-described effects, there may be other effects.

BEST MODE

Figure 1:
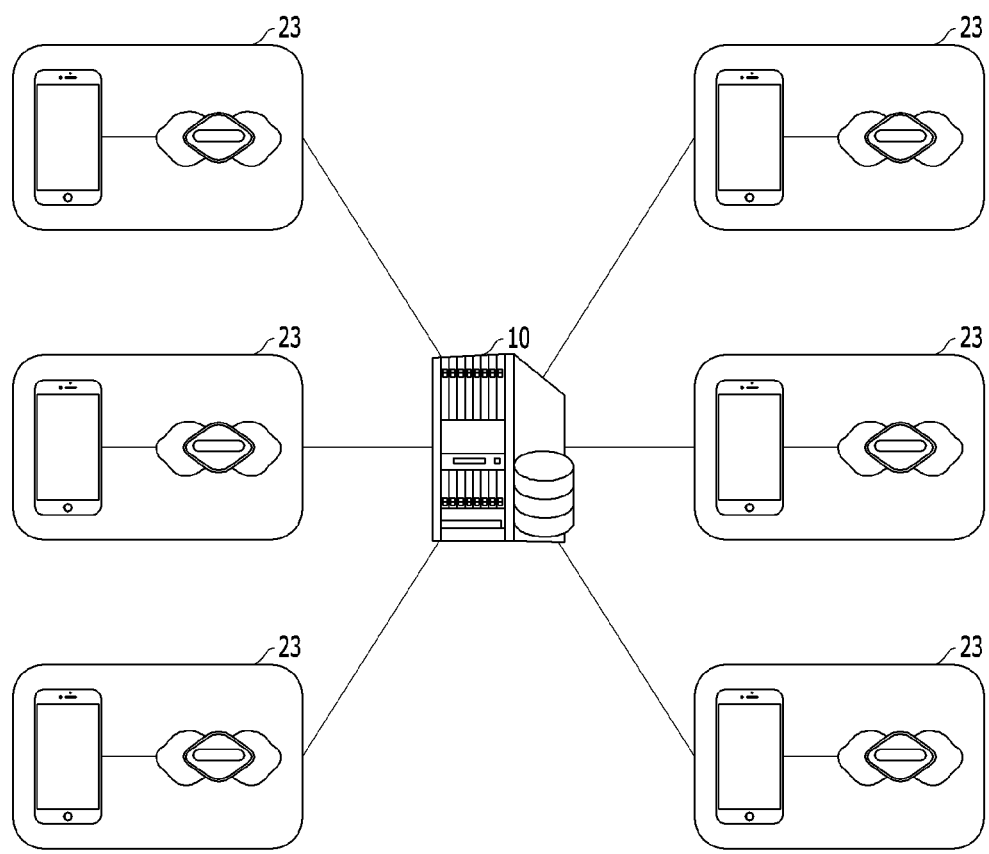
FIG. 1 is a schematic diagram of a real-time multi-monitoring apparatus using an electrocardiograph according to an exemplary embodiment of the present disclosure.

Hereinafter, the exemplary embodiment of the present disclosure will be described in detail with reference to the accompanying drawings so that those with ordinary skill in the art to which the present disclosure pertains will easily be able to embody the present disclosure. However, the present disclosure can be realized in various different forms, and is not limited to the embodiments described herein. Accordingly, in order to clearly explain the present disclosure in the drawings, portions not related to the description are omitted. Like reference numerals designate like elements throughout the specification.

In the whole specification of the present disclosure, when it is described that an element is "coupled" to another element, the element may be "directly coupled" to the other element or "electrically coupled" or "indirectly coupled" to the other element through a third element.

In the whole specification of the present disclosure, when one member is located "on", "above", "on an upper portion", "below", "under", and "on a lower portion" of the other member, the member may be adjacent to the other member or a third member may be disposed between the above two members.

In the whole specification of the present disclosure, when a part "includes" a component, this means that another element can be further included instead of excluding other elements unless any particular opposite description exists.

In the related art, a relay type communication device stores and displays ECG data in a monitoring server. (ECG patch, a relay-type communication device, a monitoring server, a remote viewer, a storage) is also configured by an ECG patch, a smart phone, a web server, and a web client and biosignals for an ECG, a pulse, and stress are utilized. It is possible to see personal health records of acquaintances or family members, but it is difficult to see the personal health records for many people.

That is, the Holter monitor of the related art cannot store the record in real-time and the patient monitor does not perform the multi-monitoring. An event recorder stores an event only when the event occurs. According to the related art technique, a modem is provided in an ECG measurement device and only when an abnormal ECG signal is generated, the signal is transmitted to a monitoring server. However, a high performance process is required for a real-time signal processing algorithm so that it is difficult to carry due to the problem in a size and a power consumption. Further, there is a problem in that the real-time signal processing algorithm is for the personal health record so that it is suitable for 1:1, but is vulnerable to one to many.

Hereinafter, for the convenience of description, the real-time multi-monitoring apparatus using an electrocardiograph is referred to as this apparatus 10.

Figure 2:
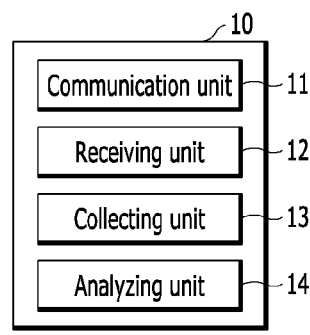
FIG. 2 is a schematic block diagram of a real-time multi-monitoring apparatus using an electrocardiograph according to another exemplary embodiment of the present disclosure.
Figure 3:
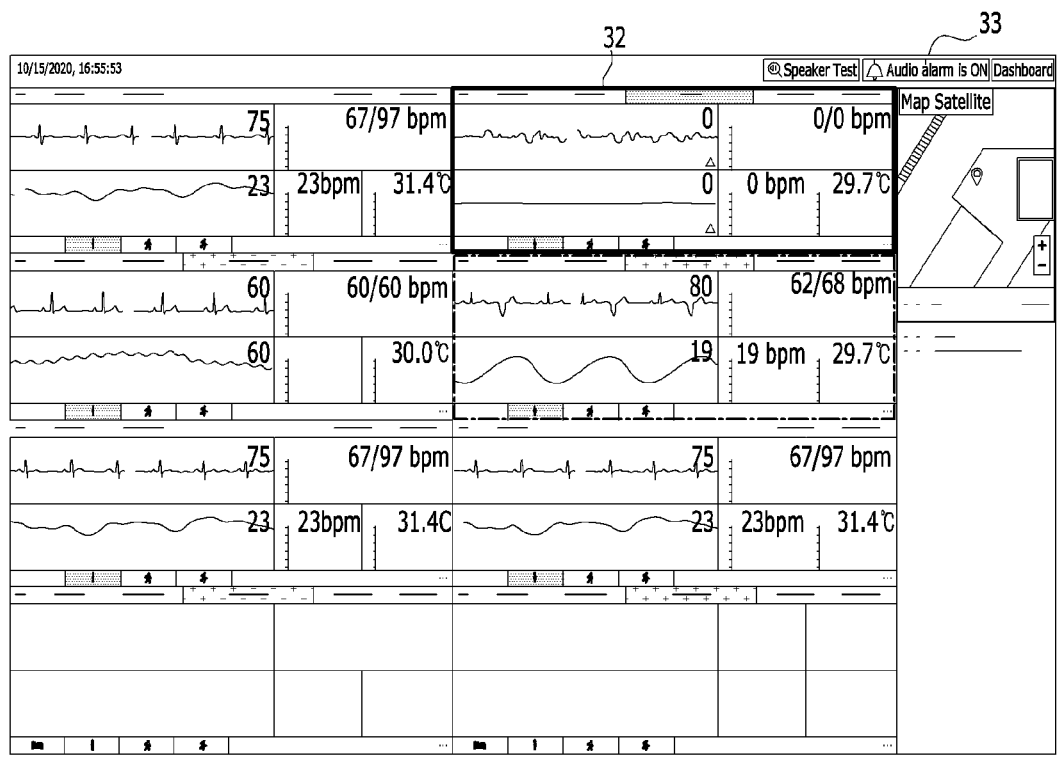
FIG. 3 is a view schematically illustrating a web client output screen of a real-time multi-monitoring apparatus using an electrocardiograph according to an exemplary embodiment of the present disclosure.

FIG. 1 is a schematic diagram of a real-time multi-monitoring apparatus using an electrocardiograph according to an exemplary embodiment of the present disclosure. FIG. 2 is a schematic block diagram of a real-time multi-monitoring apparatus using an electrocardiograph according to another exemplary embodiment of the present disclosure. FIG. 3 is a view schematically illustrating a web client output screen of a real-time multi-monitoring apparatus using an electrocardiograph according to an exemplary embodiment of the present disclosure.

This apparatus 10 is configured by a smart phone application which shows data measured from a terminal which measures an ECG, respiration, a posture, and a body temperature of a user via a wired/wireless communication to the user, a web server which stores data, and a web client which may perform multi-monitoring. According to the multi-monitoring, up to 728 people may be watched on one screen through one web client in real-time and more users may be watched as the number of web clients is increased.

According to the exemplary embodiment of the present disclosure, this apparatus 10 may include an electrocardiograph, a user terminal, a web server, and a web client. The electrocardiograph may measure biometric information of the user. The biometric information may include an ECG, respiration, a posture, and a body temperature. The user terminal may output the biometric information measured by the electrocardiograph. The user terminal may output the measured biometric information from the electrocardiograph which measures an ECG, respiration, the posture, and the body temperature of the user, by means of network communication (wired/wireless communication). The web server may be connected to any one of the plurality of electrocardiographs via the network. Further, the web server may store a plurality of biometric information measured by the plurality of electrocardiographs. The web client may perform multi-monitoring on the plurality of biometric information stored in the web server.

Referring to FIG. 1, this apparatus 10 may be connected to the plurality of electrocardiographs and the user terminal via the network. Further, each of the plurality of electrocardiographs may be connected to the user terminal.

Hereinafter, a first electrocardiograph which is attached to a part of the body of the first user to measure a biometric signal and a first user terminal which is carried by the first user connected to the first electrocardiograph may be differently referred to as a first monitoring device 21.

In FIG. 1, only six monitoring devices are illustrated for the convenience of description, but the present disclosure is not limited thereto. For example, the user terminal downloads and installs an application program provided by this apparatus 10 and data, contents, and various communication signals may be transmitted and received between this apparatus 10 and the monitoring device by means of the installed application.

The user terminal is a device which interworks with this apparatus 10 via the network, and for example, may be all kinds of wireless communication devices such as a smart phone, a smart pad, a tablet PC, a personal communication system (PCS), a global system for mobile communication (GSM), a personal digital cellular (PDC), a personal handyphone system (PHS), a personal digital assistant (PDA), an international mobile communication (IMT)-2000, code division multiple access (CDMA)-2000, W-code division multiple access (W-CDMA), and a wireless broadband internet (Wibro) terminal and fixed terminals such as a desktop computer and a smart TV.

An example of the network for sharing information between this apparatus 10 and the plurality of monitoring devices 21 to 26 may include a 3rd generation partnership project (3GPP) network, a long term evolution (LTE) network, a 5G network, a world interoperability for microwave access (WIMAX) network, wired/wireless Internet, a local area network (LAN), a wireless local area network (wireless LAN), a wide area network (WAN), a personal area network (PAN), a Bluetooth network, a WiFi network, a near field communication (NFC) network, a satellite broadcasting network, an analog broadcasting network, and a digital multimedia broadcasting (DMB) network, but are not limited thereto.

For example, the first electrocardiograph and the first user terminal may be connected via wireless communication. An example of the wireless communication may include Bluetooth, ZigBee, and iBeacon. The first electrocardiograph may acquire biometric signal information of the first user to transmit (provide) the acquired biometric signal information to the first user terminal. The first user terminal may transmit (provide) the biometric signal information transmitted (provided) from the first electrocardiograph to this apparatus 10 via the network.

According to the exemplary embodiment of the present disclosure, the electrocardiograph is formed as a patch type to be attached to a part (for example, a chest) of the body of the user to measure biometric signal information. As another example, the electrocardiograph may be worn on a part of the body (for example, wrist) of the user to extract second biometric information (for example, ECG) using the first biometric information (for example, photoplethysmogram (PPG)) which is measured only from a hand (for example, a left wrist). For example, a biometric signal measuring device 20 is formed as a watch type such as Apple watch to be worn on a wrist, which is a part of the body of the user to collect biometric information (ECG or PPG). Further, the electrocardiograph is a wearable device to measure biometric information such as an electrocardiogram, respiration, a body temperature, a posture, an ECG, and PPG. The wearable device may include a patch, a smart watch, clothing, a belt (worn on a chest or waist) ring, or a stick.

Referring to FIG. 2, this apparatus 10 may include a communication unit 11, a receiving unit 12, a collecting unit 13, and an analyzing unit 14. However, the configuration of this apparatus 10 is not limited thereto. For example, this apparatus 10 may store biometric information collected from each of the plurality of electrocardiographs in the database.

According to the exemplary embodiment of the present disclosure, the communication unit 11 may be connected to at least any one of the plurality of electrocardiographs via the network. For example, as illustrated in FIG. 1, the communication unit 11 may be connected to at least any one of the plurality of electrocardiographs and the plurality of user terminals 21 to 26 via the network. Further, the communication unit 11 may be connected to at least any one of the plurality of electrocardiographs which is attached to a part of the body of the user who is required to be monitored to measure the biometric signal. As another example, the communication unit 11 may be connected to at least any one of the plurality of electrocardiographs which is worn on the part of the body of the user who is required to be monitored to measure the biometric signal. The electrocardiograph which is worn on the part of the body of the user to measure the biometric signal may be formed as a watch type.

Further, the electrocardiograph which is connected to the communication unit 11 via the network communication is changed to a connected state and may transmit the collected biometric signal information in response to the connected state. In other words, when the communication unit 11 is connected to at least any one of the plurality of electrocardiographs via the network communication, the communication unit 11 may receive (transmit) the biometric signal information which is collected by the collecting unit 13.

In the meantime, the communication unit 11 may determine a communication enable state or disable state of the network with at least any one of the plurality of electrocardiographs. When the determination result is the communication disable state of the network, the electrocardiograph may transmit the collected biometric signal information to the user terminal which is linked to the electrocardiograph. The user terminal temporarily stores the biometric signal information collected by the electrocardiograph and when the communication unit 11 and the electrocardiograph are in the network communication enable state, may transmit the temporarily stored biometric signal information.

According to the exemplary embodiment of the present disclosure, the receiving unit 12 may receive identification information of the user connected to the electrocardiograph to identify the plurality of electrocardiographs. The user identification information may include name, age, gender, and medical record information, but is not limited thereto.

According to the exemplary embodiment of the present disclosure, the collecting unit 13 may collect biometric signal information from the plurality of electrocardiographs. The collecting unit 13 may collect the biometric signal information from at least any one of the plurality of electrocardiographs which is determined to be a communication enable state of the network by the communication unit 11. For example, when the communication unit 11 determines a communication enable state with a first electrocardiograph 21, a second electrocardiograph 22, and a third electrocardiograph 23, the biometric signal information may be collected from the first electrocardiograph 21, the second electrocardiograph 22, and the third electrocardiograph 23. In contrast, when the communication unit 11 determines a communication disable state with a fourth electrocardiograph 24, a fifth electrocardiograph 25, and a sixth electrocardiograph 26, the fourth electrocardiograph 24, the fifth electrocardiograph 25, and the sixth electrocardiograph 26 may transmit (provide) the collected biometric signal information to the user terminals linked to the fourth electrocardiograph 24, the fifth electrocardiograph 25, and the sixth electrocardiograph 26, respectively. Thereafter, when the communication unit 11 and the fourth electrocardiograph 24, the fifth electrocardiograph 25, and the sixth electrocardiograph 26 are determined (changed) to be a communication enable state, the collecting unit 13 may collect the biometric signal stored in the user terminals linked to the fourth electrocardiograph 24, the fifth electrocardiograph 25, and the sixth electrocardiograph 26, respectively, and biometric signal information which is collected after the communication enable state.

The collecting unit 13 may store the biometric signal information collected from the plurality of electrocardiographs in the database so as to be linked with the identification information of the user received from the receiving unit 12. The collecting unit 13 stores (manages) the plurality of biometric signal information to be linked with the identification information of the user received from the receiving unit 12 so that the monitoring personalized for each user (patient) may be performed.

According to the exemplary embodiment of the present disclosure, the analyzing unit 14 may analyze a health condition in consideration of predetermined reference information which is defined for each user and biometric signal information collected from the plurality of electrocardiographs.

Here, the predetermined reference information which is defined for each user may be a default setting value generated so as to correspond to each of the plurality of activity modes by standardizing the plurality of biometric information of the user collected for a predetermined time. The plurality of activity modes may include activities such as exercise, sleep, games, walking, and stress.

The analyzing unit 14 generates a user's personal default setting value, rather than standard information of the plurality of users, so that when the change in the activity of the user and bio change, that is, an abnormal signal (for example, cardiac arrest, hyperventilation, sleep apnea, and fall) is detected, the risk situation may be more quickly predicted (transmitted). Further, the analyzing unit 14 analyzes a health condition of each user based on predetermined reference information which is defined for each of the plurality of users to individually monitor prognostic symptoms of health risk situations.

Further, the analyzing unit 14 may generate the user's personal default setting value in consideration of a lowest value, a highest value, and a changed value of the biometric information of the user which is generated in response to the plurality of activity modes. For example, when the user performs a specific exercise (for example, running), a setting value of biometric information, which is collected biometric information, such as ECG, PPG, a respiration rate, a pulse, a heart rate, a body temperature, and a motion may be generated.

For example, the analyzing unit 14 may standardize the plurality of biometric information of the first user collected for a predetermined time (for example, one week) to generate a user's personal basic setting value corresponding to the first activity mode (for example, sleep). In other words, the analyzing unit 14 standardizes a sleep pattern (a bedtime and a wake-up time), a respiration volume, a movement amount, heart rate information and so forth which are generated during the sleep to generate a user's default setting value related to the sleep.

According to the exemplary embodiment, the analyzing unit 14 generates a sleep signal from the acquired biometric signal (biometric information) and may estimate sleep disturbance based on the sleep signal. For example, the sleep signal may include a snoring signal, a respiration signal, a motion signal, and a heart rate signal. The analyzing unit 14 may high-pass filter the signal detected from a piezo sensor and calculates an energy signal from the high-pass filtered piezo sensor signal to generate the result as the snoring signal.

Further, the analyzing unit 14 may high-pass filter the signal detected from the motion sensor and calculates auto-correlation from the high-pass filtered biometric signal to generate the result as the heart rate signal. Further, the analyzing unit 14 may low-pass filter the signal detected from the motion sensor and smooths the low-pass filtered signal to generate the respiration signal. Further, the analyzing unit 14 may band-pass filter the signal detected from the motion sensor and generates a motion signal from a signal magnitude area (SMA) of the band-pass filtered signal. For example, the high-pass filtering for generating the snoring signal from the piezo sensor signal means a biometric signal having a component of 20 Hz or higher. Further, the low-pass filtering for generating the respiration signal from the motion sensor signal means a signal which is lower than 1 Hz and the high-pass filtering for generating the heart rate signal means a signal of 1 to 30 Hz. Further, the band-pass filtering for generating the motion signal means a signal of 0.5 to 20 Hz.

Further, the analyzing unit 14 generates the sleep signal from the biometric signal (biometric information) to utilize the sleep signal as information for detecting snoring or apnea, motion, and heart rate signals during the sleep. That is, during the sleep, the vibration is generated due to sleep talking, toss and turning, or the like, as well as the snoring or apnea, so that a piezoelectric sensor and a motion sensor may detect the vibration. However, the low-pass filtering and the high-pass filtering are performed at a low band frequency and a high band frequency set to detect the snoring or the apnea so that the sleep talking or toss and turning are not misunderstood as the snoring or apnea.

In other words, the analyzing unit 14 generates the sleep signal from the biometric signal (biometric information) and a user's personal default setting value for a sleep mode which is one of a plurality of activity modes is generated in consideration of the sleep signal and when the user is determined to have a sleep apnea (OSA), alarm information is provided to the user terminal 30.

Further, the analyzing unit 14 may generate the user's personal default setting value corresponding to the plurality of activity modes in consideration of user's personal life environment information obtained from the user terminal linked to the electrocardiograph, medical record information obtained from an external server, and a plurality of biometric information collected for a predetermined time. The analyzing unit 14 may collect various information generated based on the user, such as user's personal life environment information, medical record information, and biometric information to set the user's personal default setting value in consideration of a user's existing medical history, occupation as an athlete, and genetic heredity.

The user's personal life environment information may include a smoking amount, a drinking amount, lifestyle, exercise status, a residential area, user's eating habit analysis information, a frequency of eating out, a number of times of delivery food orders, a public transportation usage record, user's credit and debit card usage history analysis information, and commercial area analysis information of the area in which the user resides. Further, the analyzing unit 14 may acquire user's personal information from the user terminal linked to the electrocardiograph. The personal information may include the gender, the age, the height, the weight, the race, the nationality, and the occupation of the user. Further, the medical record information may include a medical image storage transmission system (PACS), an electronic medical record (EMR), an electronic health record (EHR) PHR, HIS, OCS, mobile EMR, and smartphone EMR. That is, the medical record information may be user's personal health information provided from a hospital server (terminal).

Further, when there is a waveform which satisfies a predetermined feature condition in the biometric signal information acquired by the collecting unit 13, the analyzing unit 14 may determine a signal corresponding to the waveform which satisfies the predetermined feature condition as a suspicious abnormal ECG signal.

For example, the analyzing unit 14 analyzes an ECG signal among the plurality of biometric signals measured from each of the plurality of electrocardiographs to determine whether a heart condition is normal or abnormal. Here, when the heart condition is normal, it may be differently represented that the user's health condition is a stable state and when the heart condition is abnormal, it may be differently represented that the user's health condition is an unstable state (for example, arrhythmia state).

The analyzing unit 14 analyzes the ECG signal among the plurality of biometric information to determine (analyze) whether the user's heart condition is normal (that is, the health state is stable) or abnormal (that is, the health state is unstable) as a state diagnostic result.

When a waveform which satisfies the predetermined feature condition is present in a waveform of the ECG signal, among the plurality of biometric information, the analyzing unit 14 may primarily determine that a signal corresponding to a waveform which satisfies the predetermined feature condition is a suspicious abnormal ECG signal. Here, the predetermined feature condition may refer to a condition for the feature that a signal belonging to a threshold range is generated during a predetermined time.

In other words, the analyzing unit 14 may primarily determine whether the suspicious abnormal ECG signal which is suspected to be an abnormal ECG signal occurs depending on whether there is a waveform in which the signal belonging to the threshold range is generated for a predetermined time, among waveforms of the ECG signal, among the plurality of biometric signal measured from each of the plurality of ECGs. Here, the threshold range may be a range set for an amplitude of the waveform of the ECG signal acquired from the collecting unit 13.

The analyzing unit 14 may determine whether there is a waveform S2 which satisfies a feature (waveform feature) that a signal belonging to the threshold range r is generated during a predetermined time t as a predetermined feature condition, among the waveforms of the ECG signal, among the plurality of biometric information measured by each of the plurality of electrocardiographs. At this time, when there is a waveform S2 which satisfies the predetermined feature condition, the analyzing unit 14 may primarily determine a signal (an electric signal) corresponding to the waveform S2 which satisfies the predetermined feature condition as the suspicious abnormal ECG signal which is likely to be an abnormal ECG signal which appears when the user's heart condition is not good.

In other words, when there is a waveform S2 in which a signal belonging to a threshold range r is generated during a predetermine time t, in the waveform of the acquired ECG signal, the analyzing unit 14 may primarily determine a signal corresponding to the waveform, that is, a signal corresponding to the waveform S2 which satisfies the predetermined feature condition as a suspicious abnormal ECG signal which is likely to be an abnormal ECG signal. Hereinafter, the threshold range r may refer to a predetermined range for a value (or a value of an electrical signal of the ECG signal) of the ECG signal measured (acquired) by each of the plurality of electrocardiographs.

Accordingly, when an electrical signal of the ECG signal which is equal to or higher than a first voltage value and is equal to or lower than a second voltage value, among the plurality of biometric information measured by each of the plurality of electrocardiographs, is generated for the predetermined time t, the analyzing unit 14 may primarily determine the signal as a suspicious abnormal ECG signal.

When a signal having the waveform S2 which satisfies the predetermined feature condition, in the ECG signal (electrical signal), among the plurality of biometric signal measured by each of the plurality of electrocardiographs, is generated, the analyzing unit 14 does not immediately determine the signal corresponding to the waveform S2 as the abnormal ECG signal (for example, the arrhythmia signal), but may primarily (temporarily) determine as a suspicious abnormal ECG signal which is likely to be an abnormal ECG signal.

Further, the analyzing unit 14 may determine whether the suspicious abnormal ECG signal is an abnormal ECG signal based on the comparison of similarity between waveform data of the plurality of abnormal ECG signals which is stored in advance in the database and waveform data of the suspicious abnormal ECG signal.

After primarily determining to be the suspicious abnormal ECG signal, the analyzing unit 14 may secondarily (that is, finally) determine whether the suspicious abnormal ECG signal is the abnormal ECG signal based on the comparison of the similarity between the waveform data of the plurality of abnormal ECG signals which is stored in advance in the database (not illustrated) and waveform data of the suspicious abnormal ECG signal. The analyzing unit 14 may provide the state diagnosis result based on the secondary determination result.

Specifically, the analyzing unit 14 may compare the similarity between each of waveform data of the plurality of abnormal ECG signals which is stored in advance in the database (not illustrated) and waveform data of the primarily determined suspicious abnormal ECG signal. With the similarity comparison, the analyzing unit 14 may determine whether there is waveform data of the abnormal ECG signal having a similarity with the waveform data of the suspicious abnormal ECG signal which exceeds a threshold similarity, among waveform data of the plurality of abnormal ECG signals.

At this time, when there is at least one waveform data of the abnormal ECG signal having a similarity which exceeds the threshold similarity, among waveform data of the plurality of abnormal ECG signals, the analyzing unit 14 may secondarily finally determine that the waveform data of the suspicious abnormal ECG signal is waveform data of the actual abnormal ECG signal. With the secondary determination, the analyzing unit 14 may finally determine (analyze) that an abnormal ECG signal is generated in an ECG signal acquired by each of the plurality of electrocardiographs.

That is, with regard to the waveform data of the suspicious abnormal ECG signal which is primarily determined, when at least one waveform data of the abnormal ECG signal having a similarity which exceeds the threshold similarity is present in the database (not illustrated), the analyzing unit 14 may secondarily (finally) determine that the primarily determined suspicious abnormal ECG signal is the abnormal ECG signal.

The analyzing unit 14 may identify a type of the arrhythmia in consideration of the primarily determined suspicious abnormal ECG signal and the secondarily (finally) determined suspicious abnormal ECG signal. The analyzing unit 14 may determine the frequency of occurrence of arrhythmias at a predetermined reference time. For example, the predetermined reference time may be 10 minutes, but is not limited thereto.

For example, referring to FIG. 3, the analyzing unit 14 may transmit the biometric signal information collected from the electrocardiograph to a manager terminal to be linked with the identification information of the user. The analyzing unit 14 compares the predetermined reference information which is defined for each user and biometric signal information collected from the plurality of electrocardiographs and in a risky situation, may output the risk information to the manager terminal.

For example, the analyzing unit 14 may analyze a health condition in consideration of the predetermined reference information of the first user and biometric signal information collected from the first monitoring device (the electrocardiograph of the first user and the first user terminal). As an analysis result, when the arrhythmia signal is included in the ECG signal of the first user, the analyzing unit 14 may transmit risk notification information to the manager terminal.

Specifically, when the ECG signal of the first user is analyzed and an arrhythmia signal 31 is included, the analyzing unit 14 issues an audio alarm 33 and when it is determined as a risky situation 32, may transmit the risk notification information to display 34 the first user's location together with the audio alarm 33.

Figure 4:
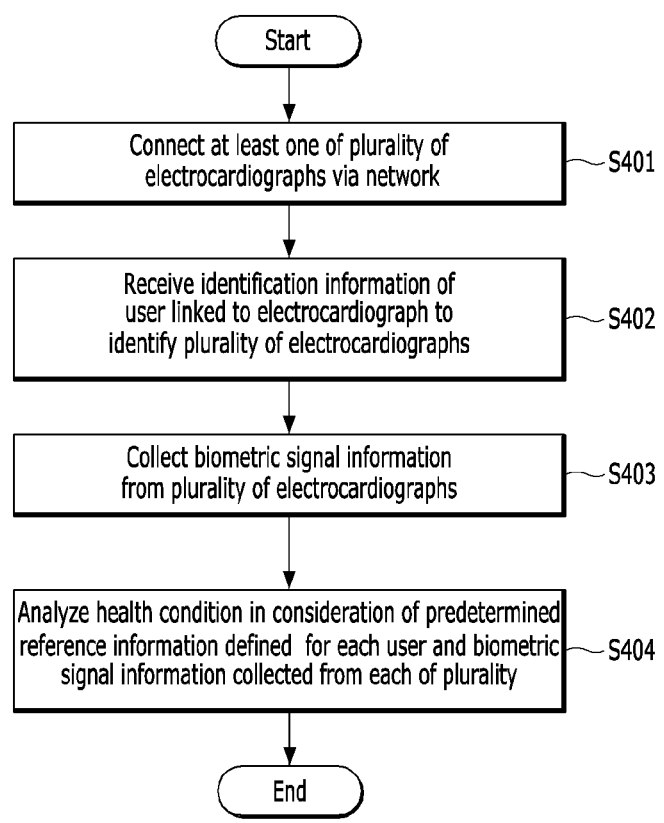
FIG. 4 is a schematic flowchart of a real-time multi-monitoring method using an electrocardiograph according to an exemplary embodiment of the present disclosure.

FIG. 4 is a schematic flowchart of a real-time multi-monitoring method using an electrocardiograph according to an exemplary embodiment of the present disclosure.

The real-time multi-monitoring method using an electrocardiograph illustrated in FIG. 4 may be performed by the real-time multi-monitoring apparatus 10 using an electrocardiograph. Accordingly, even though it is omitted, the content described for the multi-monitoring apparatus 10 using an electrocardiograph may also be applied to the description of the multi-monitoring method using an electrocardiograph in the same way.

In step S401, this apparatus 10 may be connected to any one of the plurality of electrocardiographs via the network.

In step S402, this apparatus 10 may receive identification information of the user linked to the electrocardiograph to identify the plurality of electrocardiographs.

In step S403, this apparatus 10 may collect biometric signal information from the plurality of electrocardiographs.

In step S404, this apparatus 10 may analyze a health condition in consideration of predetermined reference information which is defined for each user and biometric signal information collected from the plurality of electrocardiographs.

In the above-description, steps S401 to S404 may be further divided into additional steps or combined as smaller steps depending on an implementation example of the present disclosure. Further, some steps may be omitted if necessary and the order of steps may be changed.

The real-time multi-monitoring method using an electrocardiograph according to the exemplary embodiment of the present disclosure may be implemented in the form of program commands which may be executed by various computers to be recorded in a computer readable medium. The computer readable medium may include solely a program command, a data file, and a data structure or a combination thereof. The program instruction recorded in the medium may be specifically designed or constructed for the present disclosure or known to those skilled in the art of a computer software to be used. An example of the computer readable recording medium includes a magnetic media, such as a hard disk, a floppy disk, and a magnetic tape, an optical media, such as a CD-ROM and a DVD, a magneto-optical media, such as a floptical disk, and a hardware device, such as a ROM, a RAM, and a flash memory, specially formed to store and execute a program command. Examples of the program command include not only a machine language code which is created by a compiler but also a high level language code which may be executed by a computer using an interpreter. The hardware device may operate as one or more software modules in order to perform the operation of the present disclosure, and vice versa.

Further, the real-time multi-monitoring method using an electrocardiograph may also be implemented in the form of a computer program or an application executed by a computer which is stored in a recording medium.

The above-description of the present disclosure is illustrative only and it will be understood by those skilled in the art that the present disclosure may be easily modified to another specific type without changing the technical spirit of an essential feature of the present disclosure. Thus, it is to be appreciated that the embodiments described above are intended to be illustrative in every sense, and not restrictive. For example, each component which is described as a singular form may be divided to be implemented and similarly, components which are described as a divided form may be combined to be implemented.

The scope of the present disclosure is represented by the claims to be described below rather than the detailed description, and it is to be interpreted that the meaning and scope of the claims and all the changes or modified forms derived from the equivalents thereof come within the scope of the present disclosure.

The invention claimed is:

1. A real-time multi-monitoring apparatus using an electrocardiogram the apparatus comprising:
   a communication unit connected to an electrocardiograph via a network;
   a receiving unit configured to receive identification information of a user through the network, the user being linked to the electrocardiograph to identify a user's electrocardiograph;
   a collecting unit configured to collect biometric signal information from the electrocardiograph; and
   an analyzing unit configured to analyze a health condition in consideration of predetermined reference information defined for the user and the collected biometric signal information,
   wherein the predetermined reference information includes two or more activity modes of the user, the two or more activity modes including an exercise mode and a sleep mode, the two or more activity modes being generated based on multiple biometric information of the user, and the multiple biometric information being collected over a predetermined period,
   the analyzing unit is configured to generate default values corresponding to the two or more activity modes based on the predetermined reference information and the collected biometric signal information, and
   the analyzing unit is configured to analyze the health condition based on the generated default values and the collected biometric signal information.

2. The multi-monitoring apparatus using an electrocardiograph of claim 1, wherein the electrocardiograph is attached to a part of a body of the user.

3. The multi-monitoring apparatus using an electrocardiograph of claim 1, wherein the communication unit is configured to determine a communication enable state or a disable state of the network with the electrocardiograph and when the determination result is a communication disable state of the network, the electrocardiograph transmits the biometric signal information to a user terminal linked to the electrocardiograph.

4. The multi-monitoring apparatus using an electrocardiograph of claim 1, wherein when there is a waveform satisfies satisfying a predetermined feature condition in the collected biometric signal information, the analyzing unit is configured to determine that a signal corresponding to the waveform is a suspicious abnormal ECG signal, and determine whether the suspicious abnormal ECG signal is an abnormal ECG signal based on a similarity between waveform data of abnormal ECG signals stored in a database and waveform data of the suspicious abnormal ECG signal.

5. The multi-monitoring apparatus using an electrocardiograph of claim 1, wherein the predetermined reference information includes a default setting value generated so as to correspond to each of the two or more activity modes by standardizing the multiple biometric information.

6. The multi-monitoring apparatus using an electrocardiograph of claim 1, wherein the electrocardiograph includes two or more electrocardiographs being attached to two or more users, respectively, wherein each of the two or more users is linked to a corresponding electrocardiograph.

* * * * *